United States Patent
Feldman et al.

(10) Patent No.: US 11,176,474 B2
(45) Date of Patent: Nov. 16, 2021

(54) SYSTEM AND METHOD FOR SEMANTICS BASED PROBABILISTIC FAULT DIAGNOSIS

(71) Applicant: International Business Machines Corporation, Armonk, NY (US)

(72) Inventors: Yishai A Feldman, Tel-Aviv (IL); Segev E Wasserkrug, Haifa (IL); Evgeny Shindin, Nesher (IL); Sergey Zeltyn, Haifa (IL)

(73) Assignee: International Business Machines Corporation, Armonk, NY (US)

( * ) Notice: Subject to any disclaimer, the term of this patent is extended or adjusted under 35 U.S.C. 154(b) by 922 days.

(21) Appl. No.: 15/907,291

(22) Filed: Feb. 28, 2018

(65) Prior Publication Data
US 2019/0266506 A1    Aug. 29, 2019

(51) Int. Cl.
*G06N 7/00* (2006.01)
*G01R 31/28* (2006.01)
*G06N 20/00* (2019.01)
*G06F 40/30* (2020.01)
*G16H 50/20* (2018.01)

(52) U.S. Cl.
CPC ......... *G06N 7/005* (2013.01); *G01R 31/2825* (2013.01); *G06F 40/30* (2020.01); *G06N 20/00* (2019.01); *G16H 50/20* (2018.01)

(58) Field of Classification Search
CPC ........ G06N 20/00; G06N 7/005; G06N 5/022; G06N 99/005; G06F 40/30; G06F 40/279; G06F 17/2785; G16H 50/20; G16H 40/40; G01R 31/2825
USPC ............................................. 706/12
See application file for complete search history.

(56) References Cited

U.S. PATENT DOCUMENTS

| | | | | |
|---|---|---|---|---|
| 2002/0019870 | A1* | 2/2002 | Chirashnya | H04L 41/142 709/224 |
| 2005/0015217 | A1* | 1/2005 | Weidl | G05B 23/0281 702/185 |

(Continued)

OTHER PUBLICATIONS

Cai, "Bayesian Networks in Fault Diagnosis", IEEE Transactions on Industrial Informatics, vol. 13, No. 5, Oct. 2017. (Year: 2017).*

(Continued)

*Primary Examiner* — Dave Misir
(74) *Attorney, Agent, or Firm* — Gregory J Kirsch

(57) ABSTRACT

A system for generating a statistical model for fault diagnosis comprising at least one hardware processor, adapted to: extract a plurality of structured values, each associated with at least one of a plurality of semantic entities of a semantic model or at least one of a plurality of semantic relationships of the semantic model, from structured historical information organized in an identified structure and related to at least some of a plurality of historical events, the semantic model represents an ontology of an identified diagnosis domain, each of the plurality of semantic entities relates to at least one of a plurality of domain entities existing in the identified diagnosis domain, and each of the plurality of semantic relationships connects two of the plurality of semantic entities and represents a parent-child relationship therebetween; extract a plurality of unstructured values, each associated with at least one of the plurality of semantic entities.

11 Claims, 10 Drawing Sheets

(56) References Cited

U.S. PATENT DOCUMENTS

| | | | | |
|---|---|---|---|---|
| 2005/0132253 A1* | 6/2005 | Gail | ................... | G06F 11/0709 |
| | | | | 714/25 |
| 2005/0234973 A1* | 10/2005 | Zeng | ....................... | G06N 5/00 |
| 2008/0201280 A1* | 8/2008 | Martin | ................... | G06N 20/00 |
| | | | | 706/12 |
| 2010/0131438 A1* | 5/2010 | Pandya | ................. | G16H 50/20 |
| | | | | 706/12 |
| 2013/0197938 A1* | 8/2013 | Bayouk | ................. | G16H 10/60 |
| | | | | 705/3 |
| 2013/0262322 A1* | 10/2013 | Kwon | .................... | D06F 34/28 |
| | | | | 705/305 |
| 2014/0142760 A1* | 5/2014 | Drees | .................... | G05B 15/02 |
| | | | | 700/275 |
| 2014/0279729 A1* | 9/2014 | Delaney | ................ | G06N 20/00 |
| | | | | 706/12 |
| 2014/0333322 A1* | 11/2014 | Kabler | .................. | G01D 4/008 |
| | | | | 324/511 |
| 2015/0317337 A1* | 11/2015 | Edgar | ................... | G16H 50/70 |
| | | | | 707/751 |
| 2016/0041070 A1* | 2/2016 | Wascat | .................. | G01M 7/00 |
| | | | | 702/183 |
| 2019/0171669 A1* | 6/2019 | Patankar | .............. | G01M 17/00 |

OTHER PUBLICATIONS

Yongli, "Bayesian Networks-Based Approach for Power Systems Fault Diagnosis", IEEE Transactions on Power Delivery, vol. 21, No. 2, Apr. 2006. (Year: 2006).*

Lo, "Bayesian Network for Fault Diagnosis", 2003. (Year: 2003).*

\* cited by examiner

SYSTEM AND METHOD FOR SEMANTICS BASED PROBABILISTIC FAULT DIAGNOSIS

BACKGROUND

The present invention, in some embodiments thereof, relates to a probabilistic fault diagnosis system and, more specifically, but not exclusively, to a system for probabilistic diagnosis of a fault in an electrical appliance.

Diagnosis is a determining or analysis of a cause or nature of a problem or situation. Diagnosis may be medical, determining the nature and circumstances of a diseased condition in a person or an animal. Diagnosis may be related to a problem or fault in a device or machine, for example an electrical appliance such as a refrigerator, a dish washer or an audio player. Diagnosis may be related to a problem or fault in a technical system such as an electrical power system or a computer system. Diagnostics refers to the discipline or practice of diagnosis. In diagnostics there is a need to answer the question "Which fault occurred?" based on one or more observed symptoms. A diagnosis process involves reasoning about cause and effect, as well as understanding joint probabilities and understanding which additional evidence can improve diagnosis. In some domains, for example the medical domain and diagnosing a device or machine, this question cannot always be answered with 100% confidence. Some diagnosis procedures quantify a probability, or a likelihood, of a possible fault's occurrence given an identified plurality of observed symptoms.

There exists computerized diagnosis systems. A computerized diagnosis system is typically adapted to diagnose a fault or a problem in an identified domain. For example, one computerized diagnosis system may be adapted to diagnose a medical problem whereas another computerized diagnosis system may be adapted to diagnose a fault in an electrical appliance. Some computerized diagnosis systems use probabilistic reasoning, outputting, for an input comprising a description of a plurality of observed symptoms, a plurality of possible problems, each with a probability of likelihood of occurrence given the plurality of observed symptoms.

SUMMARY

It is an object of the present invention to provide a system and a method for generating a statistical model for use in a fault diagnosis system.

The foregoing and other objects are achieved by the features of the independent claims. Further implementation forms are apparent from the dependent claims, the description and the figures.

According to a first aspect of the invention, a system for generating a statistical model for fault diagnosis comprises at least one hardware processor, adapted to: extract a plurality of structured values, each associated with at least one of a plurality of semantic entities of a semantic model or at least one of a plurality of semantic relationships of the semantic model, from structured historical information organized in an identified structure and related to at least some of a plurality of historical events, the semantic model represents an ontology of an identified diagnosis domain, each of the plurality of semantic entities relates to at least one of a plurality of domain entities existing in the identified diagnosis domain, and each of the plurality of semantic relationships connects two of the plurality of semantic entities and represents a parent-child relationship therebetween; extract a plurality of unstructured values, each associated with at least one of the plurality of semantic entities or the plurality of semantic relationships, from unstructured historical free text information related to at least some of the plurality of historical events; generate input data to train a statistical model, derived from the semantic model, from the plurality of structured values and the plurality of unstructured values; train the statistical model by inputting thereto the input data; and output the statistical model for use in a system for processing digital data comprising a plurality of representations of a plurality of observations related to the identified diagnosis domain, each representation selected from a group comprising a digital representation and a textual representation for the purpose of diagnosing a fault in a diagnosable entity of the identified diagnosis domain.

According to a second aspect of the invention, a method for generating a statistical model for fault diagnosis of an electrical appliance comprises: extracting a plurality of structured values, each associated with at least one of a plurality of semantic entities of a semantic model or at least one of a plurality of semantic relationships of the semantic model, from structured historical information organized in an identified structure and related to at least some of a plurality of historical events, the semantic model represents an ontology of an identified diagnosis domain, each of the plurality of semantic entities relates to at least one of a plurality of domain entities existing in the identified diagnosis domain, and each of the plurality of semantic relationships connects two of the plurality of semantic entities and represents a parent-child relationship therebetween; extracting a plurality of unstructured values, each associated with at least one of the plurality of semantic entities or the plurality of semantic relationships, from unstructured historical free text information related to at least some of the plurality of historical events; generating input data to train a statistical model, derived from the semantic model, from the plurality of structured values and the plurality of unstructured values; training the statistical model by inputting thereto the input data; and outputting the statistical model for use in a system for processing digital data comprising a plurality of representations of a plurality of observations related to the identified diagnosis domain, each representation selected from a group comprising a digital representation and a textual representation, for the purpose of diagnosing a fault in a diagnosable entity of the identified diagnosis domain.

According to a third aspect of the invention, a system for diagnosing a fault in an electrical appliance comprises at least one hardware processor, adapted to: receive a statistical model, generated by: extracting a plurality of structured values, each associated with at least one of a plurality of semantic entities of a semantic model or at least one of a plurality of semantic relationships of the semantic model, from structured historical information organized in an identified structure and related to at least some of a plurality of historical electrical appliance events, the semantic model represents an ontology of an identified diagnosis domain, each of the plurality of semantic entities relates to at least one of a plurality of domain entities existing in the identified diagnosis domain, and each of the plurality of semantic relationships connects two of the plurality of semantic entities and represents a parent-child relationship therebetween; extracting a plurality of unstructured values, each associated with at least one of the plurality of semantic entities or the plurality of semantic relationships, from unstructured historical free text information related to at least some of the plurality of historical electrical appliance events; generating input data to train a statistical model, derived from the semantic model, from the plurality of structured values and the plurality of unstructured values; and training the statistical model by inputting thereto the input data; apply the statistical model to digital data comprising a plurality of representations of a plurality of observations related to the fault in the electrical appliance, each representation selected from a group consisting of a binary representation and a textual representation, to identify one or more possible problems related to the fault; and output result digital data representing the one or more possible problems.

With reference to the first and second aspects, in a first possible implementation of the first and second aspects of the present invention, the identified diagnosis domain is diagnosis of an electrical appliance, the diagnosable entity is the electrical appliance, the plurality of historical events is a plurality of historical electrical appliance events, and each of the plurality of semantic entities relates to at least one of a group consisting of: the electrical appliance's structure, the electrical appliance's functionality, and the electrical appliance's environment. Optionally, the identified structure comprises a plurality of component identifiers of one or more components of the electrical appliance. Using a plurality of semantic entities related to an electrical appliance's structure and/or functionality and/or environment may facilitate generating a statistical model relevant to diagnosing an electrical appliance.

With reference to the first and second aspects, in a second possible implementation of the first and second aspects of the present invention, some of the plurality of semantic entities are each a member of a group of identified semantic entities consisting of: at least one observable phenomenon (a symptom), at least one dysfunction (a problem), at least one factor influencing a probability of a structural or functional relationship between two of the plurality of ontology entities (an influencing-factor), at least one symptom detail (an issue), and at least one location; and each of the plurality of semantic relationships is a member of a group of identified parent-child relationships consisting of: a causes relationship, a manifests relationship, an influences relationship, and a location-of relationship. Information relevant to diagnosis of a fault may be classified according to these semantic entity categories. Optionally, each causes relationship of the group of identified parent-child relationships connects a parent problem of the group of identified semantic entities with a child problem of the group of identified semantic entities, each manifests relationship of the group of identified parent-child relationships connects a parent problem of the group of identified semantic entities with a child symptom of the group of identified semantic entities, and each influences relationship of the group of identified parent-child relationships connects a parent influencing-factor of the group of identified semantic entities with a child problem of the group of identified semantic entities or a child symptom of the group of identified semantic entities. Semantic relationships relevant to diagnosing a fault may be described using such relationships. Using this set of relationships may facilitate mapping to a statistical model and enable use of a statistical model for diagnosis. Optionally, each location-of relationship of the group of identified parent-child relationships connects a parent issue of the group of identified semantic entities with a child location of the group of identified semantic entities, and some of the group of identified semantic entities, each selected from a group comprising a symptom of the group of identified semantic entities and a problem of the group of identified semantic entities, is mapped to a group consisting of one or more pairs of semantic entities of the group of identified semantic entities, each pair consisting of an issue of the group of identified semantic entities and a location of the group of identified semantic entities connected by a location-of relationship of the group of identified parent-child relationships. Mapping some semantic entities to one or more pairs, each of a related issue and location, may facilitate identification of more problems and/or symptoms in free text by a natural language processing method than when the free text is processed without such a mapping.

With reference to the first and second aspects, or the second implementation of the first and second aspects, in a third possible implementation of the first and second aspects of the present invention, the statistical model comprises a plurality of nodes, each representing one of some of the plurality of semantic entities, connected by a plurality of edges, each representing one of some of the plurality of semantic relationships. The some of the plurality of semantic entities are each one of a group consisting of: a problem of the group of identified semantic entities, a symptom of the group of identified semantic entities, and an identifying-factor of the group of identified semantic entities. The some of the plurality of semantic relationships are each one of a group consisting of: a causes relationship of the group of identified parent-child relationships, a manifests relationship of the group of identified parent-child relationships, an influences relationship of the group of identified parent-child relationships. Using a statistical model representing these semantic entities may facilitate using the statistical model for diagnosis of a fault in a diagnosis domain the semantic entities are related to. Optionally, each of the plurality of nodes has a Boolean occurrence value indicating an occurrence of the node, every symptom node of the plurality of nodes, representing a symptom of the plurality of identified semantic entities, is assigned a local probability model defined by: identifying a plurality of manifesting parent nodes such that each is a parent node connected by a manifesting edge, representing a manifests relationship of the group of identified parent-child relationships, to the symptom node; identifying a plurality of influencing-factor parent nodes such that each is a parent node connected by an influencing-factor edge, representing an influencing-factor relationship of the group of identified parent-child relationships, to the symptom node; identifying a plurality of influencing combinations of a plurality of Boolean occurrence values of the plurality of influencing-factor parent nodes; and for each influencing combination of the plurality of influencing combinations: associating with each manifesting parent node of the plurality of manifesting parent nodes a probability that a true Boolean occurrence value of the manifesting parent node does not cause a true Boolean occurrence value of the symptom node, denoted by $\lambda_w$; associating with the symptom node a probability that the symptom node has a true Boolean occurrence value when none of the plurality of manifesting parent nodes has a true Boolean occurrence value, denoted by $\lambda_0$; and associating with the symptom node a noisy—or distribution computed by: computing a plurality of node terms by for each of the plurality of manifesting parent nodes having a true Boolean occurrence value subtracting the manifesting parent node's $\lambda_w$ from 1; multiplying the plurality of node terms to produce a parent product; computing an independent term by substituting $\lambda_0$ from 1; multiplying the parent product by the independent term to produce a node product; and subtracting the node product from 1. Optionally, training the statistical model comprises deriving values for a plurality of $\lambda_w$ and $\lambda_0$ values from the input data using methods as known in the art. Optionally, each of the plurality of nodes has a Boolean occurrence value indicating an occurrence of the node; wherein each node having a true Boolean occurrence value has a numerical value of 1, otherwise a numerical value of 0; wherein every problem node of the plurality of nodes, representing a problem of the plurality of identified semantic entities, is assigned a local probability model defined by: identifying a plurality of causing parent nodes such that each is a parent node connected by a causing edge, representing a causes relationship of the group of identified parent-child relationships, to the problem node; identifying a plurality of influencing-factor parent nodes such that each is a parent node connected by an influencing-factor edge, representing an influencing-factor relationship of the group of identified parent-child relationships, to the problem node; identifying a plurality of influencing combinations of a plurality of Boolean occurrence values of the plurality of influencing-factor parent nodes; and for each influencing combination of the plurality of influencing combinations: associating with each causing parent node of the plurality of causing parent nodes a node weight modifying the local probability model, denoted by $w_k$; associating with the problem node an independent weight modifying the local probability model, denoted by $w_0$; and associating with the problem node a logistic conditional probability distribution computed by: computing a plurality of node terms by for each of the plurality of causing parent node's multiplying the causing parent node's $w_k$ by the causing parent node's numerical value; adding the plurality of node terms to produce a parent sum; adding the parent sum to the independent term to produce a node sum; and computing a sigmoid function of the node sum. Optionally, training the statistical model comprises deriving values for a plurality of $w_k$ and $w_0$ values from the input data using methods as known in the art. Using one or more local probability models may reduce an amount of storage required for storing the statistical model and additionally or alternatively an amount of storage required for storing data for training the statistical model. In addition, using one or more local probability models may reduce a number of parameters learned when training the statistical model and thus may reduce complexity of computations in training the statistical model. Optionally the statistical model is a Bayesian network.

With reference to the first and second aspects, in a fourth possible implementation of the first and second aspects of the present invention, the at least one hardware processor is adapted to output the statistical model by storing the statistical model on a non-volatile digital storage connected to the at least one hardware processor or by sending the statistical model to at least one other hardware processor via at least one digital communication network interface connected to the at least one hardware processor. Outputting the statistical model may facilitate using a model generated by one at least one hardware processor in one or more diagnosis systems, each having another at least one hardware processor.

With reference to the first and second aspects, in a fifth possible implementation of the first and second aspects of the present invention, the at least one hardware processor is further adapted to receive the structured historical information and the unstructured historical free text information by reading the structured historical information and the unstructured historical free text information from a non-volatile digital storage connected to the at least one hardware processor. Optionally, the at least one hardware processor is further adapted to receive the structured historical information and the unstructured historical free text information via at least one digital communication network interface connected to the at least one hardware processor. Receiving historical information via at least one digital communication network interface may enable receiving historical information from another system, for example a database of a customer support system.

With reference to the first and second aspects, in a sixth possible implementation of the first and second aspects of the present invention, the identified diagnosis domain is diagnosis of a medical condition, the diagnosable entity is a patient, the plurality of historical events is a plurality of historical medical events, and each of the plurality of semantic entities relates to a medical term of a medical ontology.

With reference to the third aspects, in a first possible implementation of the third aspect of the present invention, the binary and textual representations of the plurality of observations comprise information selected from a group comprising: structured observation information organized in the identified structure and free text observation information. The at least one hardware processor is adapted to apply the statistical model to the digital data by: extracting a plurality of structured symptom values, each associated with at least one of the plurality of semantic entities or the plurality of semantic relationships, from the structured observation information; extracting a plurality of unstructured symptom values, each associated with at least one of the plurality of semantic entities or the plurality of semantic relationships, from the unstructured free text observation information; generating symptom input data from the plurality of structured symptom values and the plurality of unstructured symptom values; computing a plurality of probabilities of a plurality of suggested problems by inputting the symptom input data to the statistical model; and identifying some of the plurality of suggested problems as the one or more possible problems. Extracting a plurality of structured symptom values and a plurality of unstructured symptom values from binary and textual representations of the plurality of observations may produce input for a statistical model, which in turn may be applied to the plurality of extracted values in order to diagnose a fault. Optionally, the result digital data comprises for each of the one or more possible problems a problem description and a rank value. Providing a rank for each of the possible problems may reduce false diagnosis, and thus reduce costs, for example maintenance costs or medical treatment costs, caused due to false diagnosis. Optionally, the at least one hardware processor is adapted to output the result digital data by a method selected from a group comprising: sending at least one message on at least one digital communication network interface connected to the at least one hardware processor, and displaying one or more messages on at least one display device connected to the at least one hardware processor. Optionally, the at least one hardware processor is further adapted to: extract a plurality of structured resolution values, each associated with at least one of the plurality of semantic entities or the plurality of semantic relationships, from structured resolution information, organized in the identified structure, of resolution digital data comprising binary and textual representations of one or more resolutions of the fault of the electrical appliance; extract a plurality of unstructured resolution values, each associated with at least one of the plurality of semantic entities or the plurality of semantic relationships, from unstructured free text resolution information of the resolution digital data; generate event input data from the plurality of structured symptom values, the plurality of unstructured symptom values, the plurality of structured resolution values, and the plurality of unstructured resolutions values; and train the statistical model by inputting thereto the event input data. Training the statistical model with data collected from an event additional to the historical events may improve performance and accuracy of the statistical model in future diagnosis.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

Figure 1:
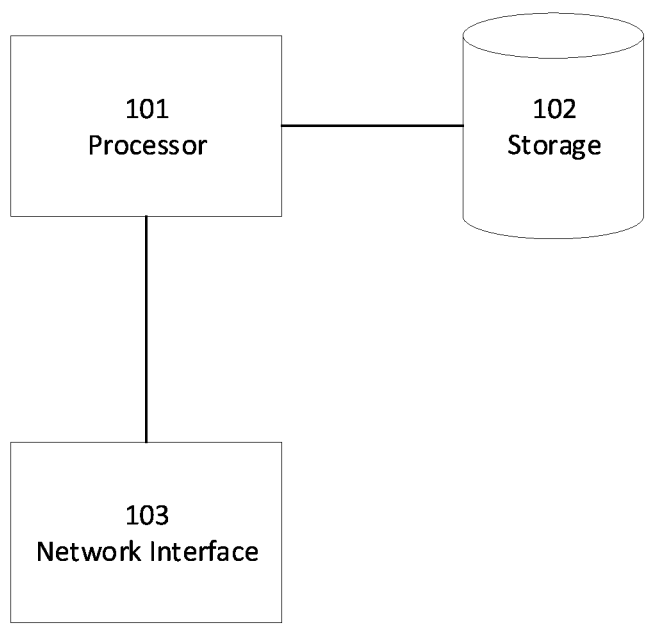
FIG. 1 is a schematic block diagram of an exemplary system for generating a statistical model, according to some embodiments of the present invention.

The present invention, in some embodiments thereof, relates to a probabilistic fault diagnosis system and, more specifically, but not exclusively, to a system for probabilistic diagnosis of a fault in an electrical appliance.

A probabilistic diagnosis system is a diagnosis system using probabilistic reasoning. Computerized probabilistic diagnosis systems facilitate incorporating expertise of more than one professional in a certain domain, and/or experience gained over a period of time, into a common expert system for the certain domain. Such expertise may comprise not only knowing which problems can be associated with which observed symptoms, but also which problems are more likely given a plurality of observed symptoms.

When building a probabilistic diagnosis system it is necessary to choose a mathematical model (a statistical model) representing one or more probabilistic relationships between a plurality of possible problems and a plurality of possible observed symptoms. In addition, it is necessary to create a domain-specific structure for the statistical model comprising a domain-specific plurality of possible dysfunctions (problems), a domain-specific plurality of observed phenomena (symptoms) and a domain-specific plurality of probabilistic relationships, and populate the statistical model with one or more probabilities. Given a plurality of observed symptoms, the statistical model may be used to compute the probabilities of the presence of various problems.

When historical data, describing a plurality of historical events, is available, the historical data may be used to calculate one or more probabilities of an occurrence of a problem, given one or more observed symptoms. Each historical event in such historical data may comprise one or more historical observed symptoms and a historical diagnosed problem. A plurality of historical observed symptoms and historical diagnosed problems may be extracted from the plurality of historical events and used to train the statistical model, populating the statistical model with the one or more probabilities.

It may be that some of the historical data is structured in an identified structure. For example, in a system for diagnosing an electrical appliance, the identified structure may comprise one or more identified error codes and one or more component identifiers. In such a system, the historical data may comprise for example one or more of: an observed identified error code and a component identifier of a faulty component. On the other hand, it may be that some of the historical data is unstructured, typically comprising free text describing one or more observed symptoms and additionally or alternatively one or more diagnosed faults. For example, in a system for diagnosing an electrical appliance, the free text may describe one or more actions performed by a technician of the appliance, such as "I cleaned the filter". In another example, the free text may describe one or more observations made by a person, such as "I saw a puddle of water under the dishwasher", "there is a clicking sound when the pump works", and "the washed laundry has grey stains". Such unstructured historical data typically cannot be used directly to train a statistical model. However, training the statistical model using information described in the unstructured historical data may increase accuracy of the one or more probabilities of the statistical model. A professional using an output of a system trained using the information described in the unstructured historical data may be able to resolve a problem faster and for a lower cost than when using an output of a less accurately trained statistical model. For example, when using a statistical model for diagnosing a medical problem, more accurate statistical model probabilities may reduce occurrences of a false diagnosis and reduce administration of ineffective treatments. In another example, when using a statistical model for diagnosing a problem in an electrical appliance, more accurate statistical model probabilities may reduce appliance downtime by expediting repair time and may reduce cost of maintenance by reducing occurrences of unnecessary component replacements due to misdiagnosis.

The present invention, in some embodiments thereof, proposes generating a statistical model for fault diagnosis in an identified domain by extracting a plurality of values from both the structured historical data and the unstructured historical data according to a semantic model describing the identified domain, and training a statistical model derived from the semantic model using input data comprising the extracted plurality of values. In some embodiments of the present invention, such a statistical model is then used in a diagnosis system for diagnosis given one or more observed symptoms by computing one or more probabilities of one or more possible problems. Using a semantic model allows incorporating unstructured historical data into a formal structure of the statistical model, making a combination of the structured historical data and the unstructured historical data available for a training process of the statistical model, improving accuracy of the statistical model's probabilities.

In addition, in some embodiments the present invention proposes further training the statistical model used in the diagnosis system using additional input data generated from the one or more observed symptoms and one or more resolution descriptions related to the one or more observed symptoms. Optionally, further training the statistical model is done continuously. Further training the statistical model using additional input data generated from one or more resolution descriptions related to the one or more observed symptoms may further improve accuracy of the statistical model's probabilities. Continuously further training the statistical model may continuously improve accuracy of the statistical model's probabilities over time, thus improving diagnosis performed using the statistical model allowing reduction of penalties incurred by misdiagnosis such as length of patient recovery time, length of appliance downtime, cost of replacement components, and length of repair time.

In some embodiments of the present invention the semantic model comprises a plurality of semantic entities, each selected from: one or more observable phenomena (symptoms), one or more dysfunctions (problems), one or more factors each influencing a probability of a structural or functional relationship between two of the plurality of nodes (influencing-factors), one or more symptom details (issues) and one or more locations. Some examples of a symptom are a fault code, "PuddleUnderAppliance", and "DishesNotClean". A dysfunction (problem) may be a condition that manifests as a symptom. In a semantic model describing fault diagnosis of an electrical appliance, some examples of a problem are a bad initialization status code, "Pipe123Cracked", and "Fuse5Disconnected". In a semantic model describing diagnosis of a medical issue an example of a problem is "MitralValveLeaking". Some examples of an influencing-factor are age of an appliance, a weather condition and a production run identifier. Some examples of an issue are "DoesNotStart" and "Leaks". Some examples of a location are a component identifier and "Appliance". In addition, in such embodiments the statistical model comprises a plurality of semantic relationships, each representing a parent-child relationship between two semantic entities of the plurality of semantic entities. Possible parent-child relationships are a causes relationship, where a child problem is caused by a parent problem, a manifests relationship, where a child symptom is manifested by a parent problem, an influences relationship, where a child symptom or a child problem is influenced by a parent influencing factor, and a location-of relationship where a child location is related to a parent issue. In addition, in such embodiments the semantic model optionally comprises a mapping identifying each of one or more symptoms and/or problems by one or more combinations of an issue and a location connected by a location-of relationship. For example, a symptom of "machine does not start" may be mapped to a combination of an issue of "does not start" connected by a location-of relationship to a location of "machine". Optionally, the mapping identifies each of one or more symptoms and/or problems by an issue. This mapping may improve accuracy of extraction of some of the plurality of values from the unstructured historical data.

In some embodiments the statistical model is a Bayesian network model. A Bayesian network is a probabilistic graphical model that represents a set of variables and their conditional dependencies via a directed acyclic graph (DAG). Each of the plurality of nodes of the DAG represents one of the set of variables, and each of the plurality of edges of the DAG represents a conditional dependency between two of the set of variables. In some embodiments of the present invention where the statistical model is a Bayesian network model, each node of a plurality of nodes of the Bayesian network model represents a Boolean occurrence variable of one of some of the plurality of semantic entities of the semantic model. In addition, in such embodiments, each edge of a plurality of edges of the Bayesian network model represents one of some of the plurality of semantic relationships of the semantic model. In such embodiments, each edge of the plurality of edges connecting two nodes of the plurality of nodes represents a conditional dependency between two Boolean occurrence variables of the two semantic entities represented by the two nodes, one node being a parent node and a second node being a child node such that a child Boolean occurrence variable represented by the child node is conditionally dependent on all parent Boolean occurrence variables represented by all parent nodes of the child node. The value of a node's Boolean occurrence variable is probabilistically independent of values of Boolean occurrence variables of other ancestor nodes besides the node's direct parents.

A Bayesian network has one or more probabilities. The one or more probabilities of a Bayesian network include for each node a table specifying a probability of each value of the node for each set of possible values for the node's parents. Such a table is called a conditional probability table (CPT). Optionally, the present invention proposes representing each node's CPT by a local probability model. An unrestricted CPT, for a node having an amount of parents denoted by n, would have $2^{n-1}$ independent entries. Using a local probability model may allow specifying fewer parameters than when specifying an unrestricted CPT. Specifying fewer parameters may reduce an amount of storage required for storing a statistical model and additionally or alternatively an amount of storage required for storing training data for training the mathematical model.

In embodiments where the statistical model's plurality of nodes and plurality of edges are defined as described above, the causes relationship and the manifests relationship have a causal nature, allowing associating with each such relationship a local probability model that satisfies a property of independence of causal influences, where an effect of each parent on a child may be specified individually and an overall CPT may be calculated from a plurality of individual influences. Non-limiting examples of a local probability model satisfying a property of independence of causal influences are a noisy—or model and a logistic conditional probability distribution.

In addition, in some embodiments the present invention proposes defining one or more formal definitions tying the statistical model's structure and probabilities to semantics of the domain according to the semantic model, and using the one or more formal definitions to expedite extraction of some of the plurality of values from the unstructured historical data. Some examples of a formal definition are a regular expression, i.e. a sequence of characters that define a search pattern, optionally defined according to the semantic model describing the identified domain, a rule mapping an identified text to a semantic entity of the statistical model's plurality of semantic entities or to a semantic relationship of the semantic model's plurality of semantic relationships, and an annotation of free text of historical unstructured data mapping an identified text to a semantic entity of the semantic model's plurality of semantic entities or to a semantic relationship of the semantic model's plurality of semantic relationships. Optionally, rule based natural language processing methods are used to extract some of the plurality of values from the unstructured historical data according to one or more rules. In addition or alternatively, machine learning techniques are optionally used to extract some of the plurality of values from the unstructured historical data according to some annotated free text of the unstructured historical data. Using machine learning techniques may facilitate capturing text that is similar but not identical to the annotated text. In addition, some machine learning techniques are capable of identifying relationships as well as entities and using such machine learning techniques facilitates extracting one or more symptom values and/or problem values according to one or more combinations of an issue and a location connected by a location-of relationship mapped by the semantic model to one or more symptoms and problems. In addition or alternatively, one or more of the plurality of values are extracted from the unstructured historical data by matching free text of the unstructured historical data with one or more regular expressions.

The plurality of semantic entities and plurality of semantic relationships may be an ontology, that is a formal naming and definition of types, properties, and interrelationships of entities that exist in a domain of discourse. The following non-limiting disclosure focuses on possible embodiments where the present invention is used in an appliance-repair domain, for fault diagnosis of an electrical appliance, and the semantic model comprises a plurality of semantic entities and semantic relationship existing in the appliance repair domain. However, the present invention is not limited to the appliance-repair domain and may be used in other domains such as medical diagnosis and technical system maintenance. In embodiments used in such another domain, the plurality of semantic entities and semantic relationships are defined according to the other domain.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing.

Computer readable program instructions described herein can be downloaded to respective computing/processing devices from a computer readable storage medium or to an external computer or external storage device via a network, for example, the Internet, a local area network, a wide area network and/or a wireless network.

The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference is now made to FIG. 1, showing a schematic block diagram of an exemplary system 100 for generating a statistical model, according to some embodiments of the present invention. In such embodiments, at least one hardware processor 101 is connected to at least one non-volatile digital storage 102. At least one storage 102 is optionally used to store a generated statistical model. Examples of a non-volatile digital storage are a hard disk and non-volatile random access memory (NVRAM). Optionally, at least one storage 102 is used to store structured historical information and in addition or alternatively unstructured historical free text information related to at least some of a plurality of historical events, for example a plurality of historical electrical appliance events, or a plurality of historical medical records. An example of a historical electrical appliance event is an appliance malfunction event, where the structured historical information comprises a component identifier of a malfunctioning component and the unstructured historical free text information comprises a description of some observed symptoms. Optionally, at least one hardware processor is connected to at least one digital communication network interface 103. Examples of a digital communication network interface are a wireless network interface or an Ethernet interface. Optionally, at least one hardware processor 101 sends the generated statistical model to another hardware processor using at least one network interface 103. Optionally, the structured historical information and in addition or alternatively the unstructured historical free text information is digital information, stored in a digital repository such as a database. Optionally, at least one hardware processor 101 receives the structured historical information and in addition or alternatively the unstructured historical free text information regarding the plurality of historical electrical appliance events via at least one network interface 103.

In order to generate a statistical model for fault diagnosis in an identified diagnosis domain, system 100 implements in some embodiments the following optional method.

Figure 2:
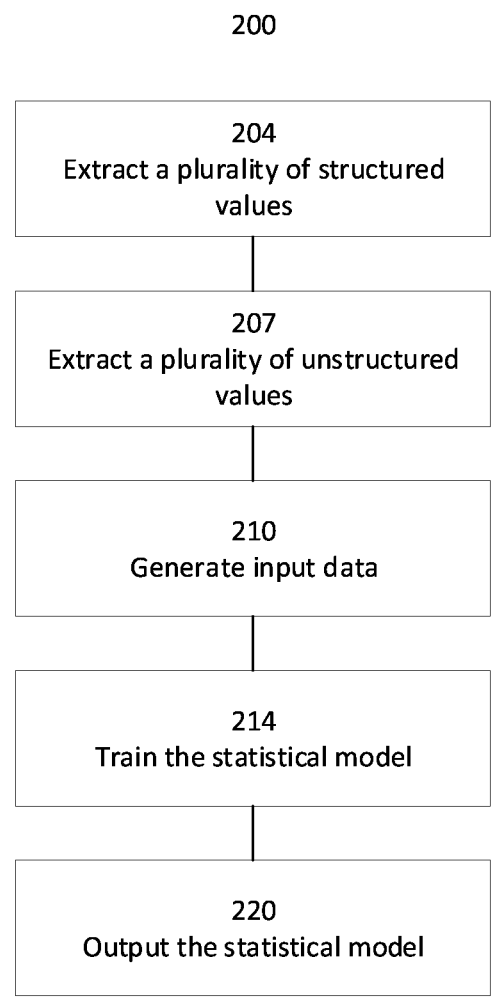
FIG. 2 is a flowchart schematically representing an optional flow of operations for generating a statistical model for fault diagnosis, according to some embodiments of the present invention.

Reference is now made also to FIG. 2, showing a flowchart schematically representing an optional flow of operations 200 for generating a statistical model for fault diagnosis, according to some embodiments of the present invention. In such embodiments, at least one hardware processor 101 uses a statistical model derived from a semantic model. The semantic model optionally represents an ontology of the identified diagnosis domain and optionally has a plurality of semantic entities, each semantic entity relates to one or more properties of the identified diagnosis domain, e.g. a plurality of domain entities existing in the identified diagnosis domain. When the identified diagnosis domain is diagnosis of an electrical appliance, some possible properties are an electrical appliance's structure, for example an identifier of a component of the electrical appliance, an electrical appliance's functionality, for example "does not start" and "leaks", and an electrical appliance's environment, for example "under the machine". When the identified diagnosis domain is diagnosis of a medical condition, some of the properties may be related to a medical term of a medical ontology such as an organ or a measured vital sign.

Optionally, each of the plurality of semantic entities is a member of a group of identified semantic entities comprising: at least one observable phenomenon (a symptom), at least one dysfunction (a problem), at least one factor influencing a probability of a structural or functional relationship between two of the plurality of semantic entities (an influencing-factor), a symptom detail (an issue), and a location. Some examples of a symptom are a fault code value, "PuddleUnderAppliance", and "DishesNotClean". Some examples of a problem are a bad initialization status code value, "Pipe123Cracked", and "Fuse5Disconnected". Some examples of an influencing-factor are age of an appliance; a weather condition value and a production run identifier. Some examples of an issue are "DoesNotStart" and "Leaks". Some examples of a location are a component identifier and "Appliance".

The semantic model optionally has a plurality of semantic relationships, each semantic relationship connecting two of the plurality of semantic entities and representing a parent-child relationship therebetween. Optionally, each of the plurality of semantic relationships is selected from a group of identified parent-child relationships comprising: a causes relationship, a manifests relationship, an influences relationship, and a location-of relationship.

Optionally, each causes relationship of the group of identified parent-child relationships connects a parent problem of the group of identified semantic entities with a child problem of the group of identified semantic entities. In an example where the diagnosis domain is diagnosis of an electrical appliance, a causes relationship may connect a parent problem of "current regulator malfunction" with a child problem of "component 123 malfunction".

Optionally, each manifests relationship of the group of identified parent-child relationships connects a parent problem of the group of identified semantic entities with a child symptom of the group of identified semantic entities. In an example where the diagnosis domain is diagnosis of an electrical appliance, a manifests relationship may connect a parent problem of "current regulator malfunction" with a child symptom of "component 123 is black".

Optionally, each influences relationship of the group of identified parent-child relationships connects a parent influencing-factor of the group of identified semantic entities with a child problem value of the group of identified semantic entities or a symptom of the group identified semantic entities. In an example where the diagnosis domain is diagnosis of an electrical appliance, an influences relationship may connect a parent influencing-factor of "machine age=20 years" with a child symptom of "component 123 is cracked".

Optionally, each location-of relationship of the group of identified parent-child relationships connects a parent issue of the group of identified semantic entities with a child location of the group of identified semantic entities. In an example where the diagnosis domain is diagnosis of an electrical appliance, location-of relationship may connect a parent issue of "does not start" with a child location of "machine". Optionally, each symptom or problem of the group of identified semantic entities is mapped to a group comprising one or more pairs of semantic entities of the group of identified semantic entities, each pair consisting of an issue of the group of identified semantic entities and a location of the group of identified semantic entities connected by a location-of relationship of the group of identified parent-child relationships. Optionally a symptom is identified by the one or more pairs the symptom is mapped to. Optionally, a symptom is identified by an issue mapped to the symptom, without a location connected to the issue.

The statistical model is optionally a Bayesian network. Optionally, the statistical model represents some of the plurality of semantic entities of the semantic model. Optionally, the statistical model represents some of the plurality of semantic relationships of the semantic model. Optionally, the statistical model comprises a plurality of nodes, each representing one of some of the plurality of semantic entities, connected by a plurality of edges, each representing one of some of the plurality of semantic relationships. Optionally, the some of the plurality of semantic entities are each one of a group comprising: a problem of the group of identified semantic entities, a symptom of the group of identified semantic entities, and an identifying-factor of the group of identified semantic entities. Optionally, the some of the plurality of semantic relationships are each one of a group consisting of: a causes relationship of the group of identified parent-child relationships, a manifests relationship of the group of identified parent-child relationships, an influences relationship of the group of identified parent-child relationships.

In 204, at least one hardware processor 101 optionally extracts a plurality of structured values from structured historical information organized in an identified structure and related to at least some of a plurality of historical events, for example historical electrical appliance events or historical medical events. When generating a statistical model for diagnosing a fault in an electrical appliance, the identified structure optionally comprises a plurality of component identifiers of one or more components of the electrical appliance. Optionally, each of the plurality of structured values is associated with at least one of the plurality of semantic entities or the plurality of semantic relationships. In 207, at least one hardware processor 101 optionally extracts a plurality of unstructured values from unstructured historical free text information related to at least some of the plurality of historical events. Optionally, each of the plurality of unstructured values is associated with at least one of the plurality of semantic entities or the plurality of semantic relationships. In 210 at least one hardware processor optionally generates input data to train the statistical model from the plurality of structured values and the plurality of unstructured values.

Optionally, some of the plurality of structured values associated with one or more symptoms of the plurality of semantic entities and, additionally or alternatively, some of the plurality of unstructured values associated with the one or more symptoms of the plurality of semantic entities are extracted according to one or more pairs consisting of an issue of the plurality of semantic entities and a location of the plurality of semantic entities mapped to the one or more symptoms. In addition, some of the plurality of structured values associated with one or more problems of the plurality of semantic entities, and additionally or alternatively some of the plurality of unstructured values associated with the one or more problems of the plurality of semantic entities, are extracted according to an issue of the plurality of semantic entities mapped to the one or more problems or one or more pairs consisting of an issue of the plurality of semantic entities and a location of the plurality of semantic entities mapped to the one or more problems.

Figure 3:
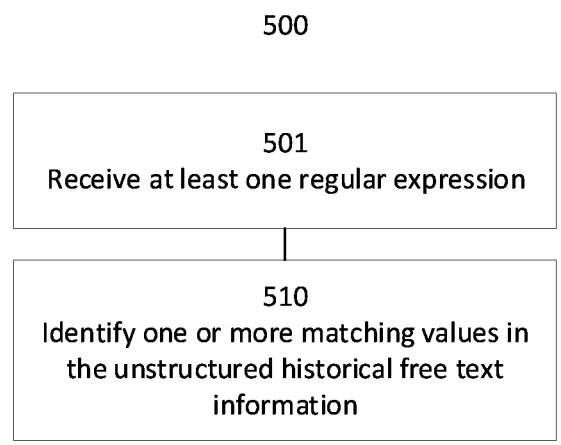
FIGS. 3, 4 and 5 are flowcharts schematically representing optional flows of operations for extracting values and generating input data, according to some embodiments of the present invention.
Figure 4:
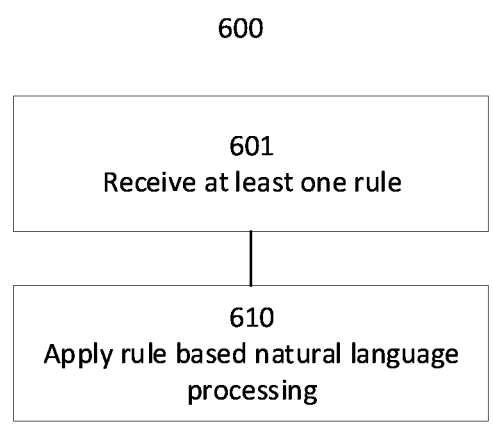
Figure 5:
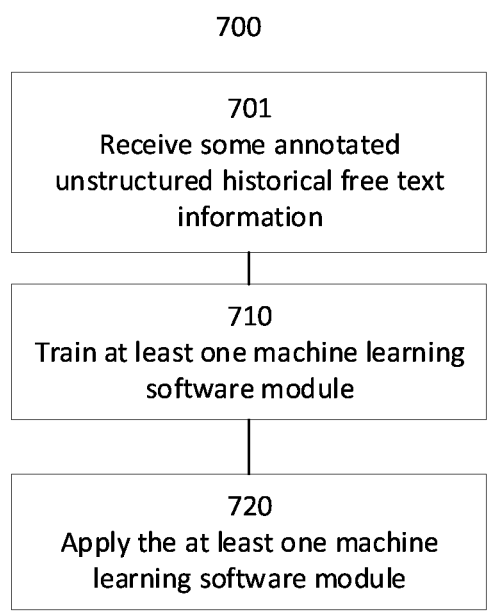

Reference is made now also to FIGS. 3, 4 and 5, showing flowcharts schematically representing optional flows of operations for extracting values and generating input data, according to some embodiments of the present invention. Reference is made now to FIG. 3, showing a flowchart schematically representing an optional flow of operations 500 for extracting unstructured values using one or more regular expressions, according to some embodiments of the present invention. In such embodiments, in 501 at least one hardware processor 101 receives at least one regular expression defined according to the plurality of semantic entities and the plurality of semantic relationships. Optionally, the at least one regular expression matches at least one value associated with at least one of the plurality of semantic entities and the plurality of semantic relationships. When the diagnosis domain is electrical appliance diagnosis, the at least one regular expression may identify a fault code of an electrical appliance. Optionally, at least one hardware processor receives the at least one regular expression by reading the at least one regular expression from at least one storage 102 or via at least one network interface 104. In 510, at least one hardware processor 101 identifies one or more matching values in the unstructured historical free text information matching the at least one regular expression.

Reference is made now to FIG. 4, showing a flowchart schematically representing optional flows of operations 600 for extracting values and generating input data, according to some embodiments of the present invention. In such embodiments, at least one hardware processor 101 receives at least one rule mapping an identified text to a semantic entity of the plurality of semantic entities or a semantic relationship of the plurality of semantic relationships. For example, a rule may map identified text "the fuse is defective" to a semantic entity of "DefectiveFuse". In 610, at least one hardware processor optionally applies rule based natural language processing methods as known in the art to the unstructured historical free text information to extract one or more unstructured values from the unstructured historical free text information and map the one or more unstructured values to one or more semantic entities of the plurality of semantic entities or one or more sematic relationships of the plurality of semantic relationships, according to the at least one rule. Examples of a rule based natural language processing method are International Business Machines (IBM) Watson Explorer Content Analytics and Stanford Core NLP Suite. Optionally, the input data comprises the mapping between the one or more unstructured values to the one or more semantic entities of the plurality of semantic entities or one or more sematic relationships of the plurality of semantic relationships.

Reference is made now to FIG. 5, showing a flowchart schematically representing optional flows of operations 700 for extracting values and generating input data, according to some embodiments of the present invention. In such embodiments, at least one hardware processor 101 receives in 701 annotated text comprising some of the unstructured historical free text information annotated with one or more annotations each mapping an identified text to a semantic entity of the plurality of semantic entities or a semantic relationship of the plurality of semantic relationships. For example an annotation may map identified text "the fuse is defective" to a semantic entity of "DefectiveFuse". In 701, at least one hardware processor 101 optionally trains at least one machine learning software module using the annotated text. Examples of a machine learning software module are IBM Watson Natural Language Understanding and RASA NLU. In 720, at least one hardware processor 101 optionally applies the at least one machine learning software module to the unstructured historical free text information to extract one or more unstructured values from the free text and map the one or more unstructured values to one or more semantic entities of the plurality of semantic entities or one or more sematic relationships of the plurality of semantic relationships. Optionally, the input data comprises the mapping between the one or more unstructured values to the one or more semantic entities of the plurality of semantic entities or one or more sematic relationships of the plurality of semantic relationships.

Reference is made again to FIG. 2. At least one hardware processor 101 in 214 optionally trains the statistical model by inputting the generated input data to the statistical model and in 220 optionally outputs the statistical model. Optionally, the trained statistical model output by at least one hardware processor 101 is used in a fault diagnosis system in order to process digital data comprising binary and textual representations of a plurality of observations for the purpose of diagnosing a fault in a diagnosable entity of the identified diagnosis domain. For example, a statistical model generated for an electrical appliance diagnosis domain may be used in a system for diagnosing a fault in an electrical appliance, and the plurality of observations may be related to the electrical appliance. In another example, a statistical model generated for a medical diagnosis domain may be used in a system for diagnosing a medical condition of a patient. Optionally, at least one hardware processor 101 outputs the statistical model by storing the statistical model on at least one storage 102 or by sending the statistical model to at least one other hardware processor via at least one network interface 103.

When the statistical model is a Bayesian network, methods as known in the art may be used to train the statistical model. In some embodiments of the present invention, for example some embodiments using a Bayesian network, a local probability model may be assigned to some of the plurality of nodes.

Figure 6A:
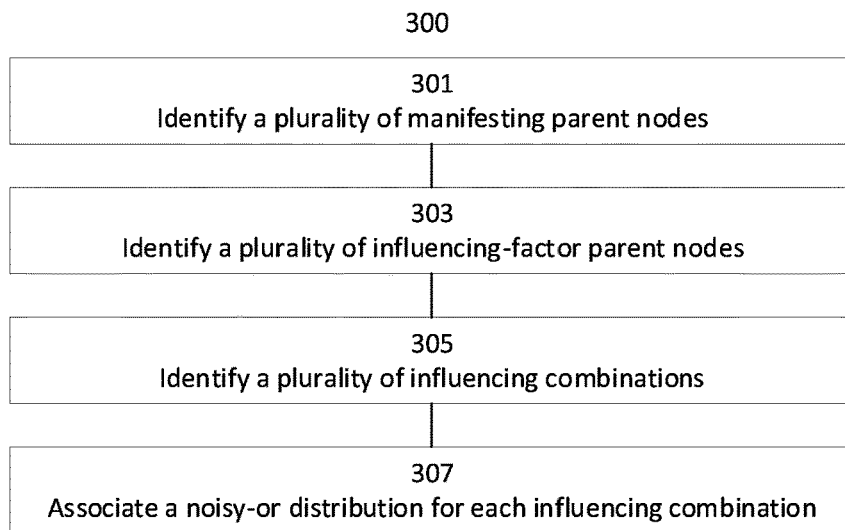
FIGS. 6A and 6B are flowcharts schematically representing an optional flow of operations for defining a local probability model.
Figure 6B:
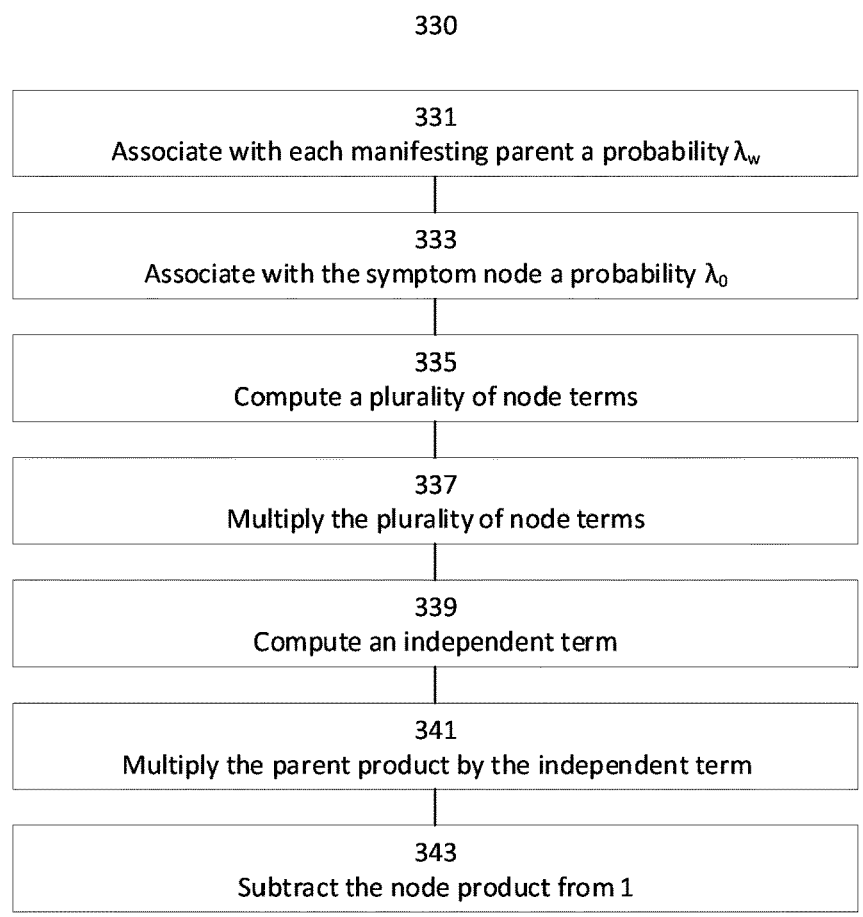

Reference is now made also to FIGS. 6A and 6B, showing flowcharts schematically representing an optional flow of operations for defining a local probability model. Reference is made to FIG. 6A, showing a flowchart schematically representing an optional flow of operations 300 for defining a local probability model for a node representing a symptom, according to some embodiments of the present invention. In such embodiments, each node of the plurality of nodes has a Boolean occurrence value indicating an occurrence of the node, and at least one hardware processor 101 assigns each node representing a symptom of the plurality of identified semantic entities a local probability model defined by in 301 optionally identifying a plurality of manifesting parent nodes, such that each is a parent node connected by a manifesting edge representing a manifests relationship of the group of identified parent-child relationships, to the symptom node, in 303 optionally identifying a plurality of influencing-factor parent nodes, such that each is a parent node connected by an influencing-factor edge representing an influencing-factor relationship of the group of identified parent-child relationships, to the symptom node, and in 305 optionally identifying a plurality of influencing combinations of a plurality of Boolean occurrence values of the plurality of influencing-factor parent nodes. Next, in 307, for each of the plurality of influencing combinations, at least one hardware processor 101 optionally associates the symptom node with a noisy—or distribution. The associated noisy—or distribution may be defined according to the following optional method. Reference is made now also to FIG. 6B, showing a flowchart schematically representing an optional flow of operations 330 for defining a noisy—or distribution, according to some embodiments of the present invention. In 331, at least one hardware processor 101 optionally associates with each manifesting parent node of the plurality of manifesting parent nodes a probability that a true Boolean occurrence value of the manifesting parent node does not cause a true Boolean occurrence value of the symptom node, denoted by $\lambda_w$, and in 333 optionally associates with the symptom node a probability that the symptom node has a true Boolean occurrence value when none of the plurality of manifesting parent nodes has a true Boolean occurrence value, denoted by $\lambda_0$. Next, at least one hardware processor 101 optionally associates with the symptom node a noisy—or distribution computed by in 335 optionally computing a plurality of node terms by for each of the plurality of manifesting parent node's having a true Boolean occurrence value subtracting the manifesting parent node's $\lambda_w$ from 1, in 337 optionally multiplying the plurality of node terms to produce a parent product, in 339 optionally computing an independent term by subtracting $\lambda_0$ from 1, in 341 optionally multiplying the parent product by the independent term to produce a node product, and in 343 optionally subtracting the node product from 1. Optionally, training the statistical model in 214 comprises deriving values for a plurality of $\lambda_w$ and $\lambda_0$ values from the input data using methods as known in the art.

Figure 7A:
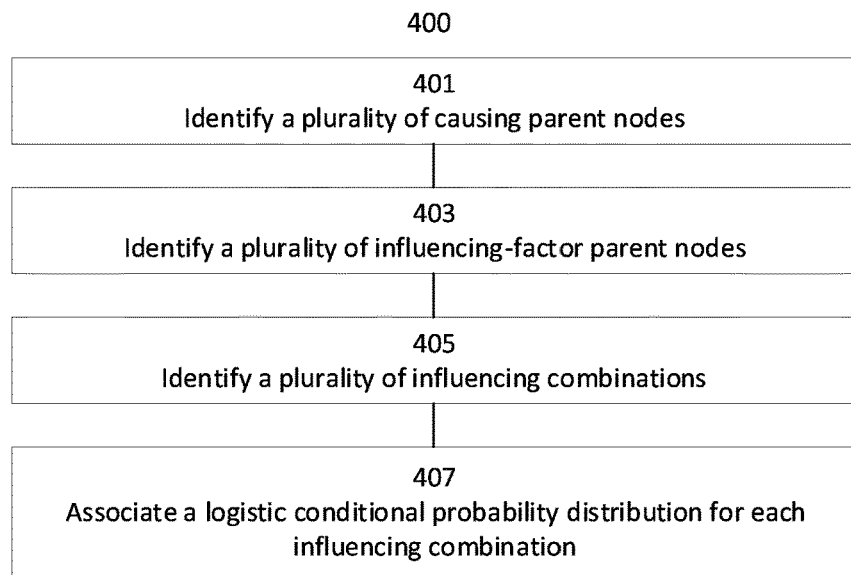
FIGS. 7A and 7B are flowcharts schematically representing another optional flow of operations for defining a local probability model.
Figure 7B:
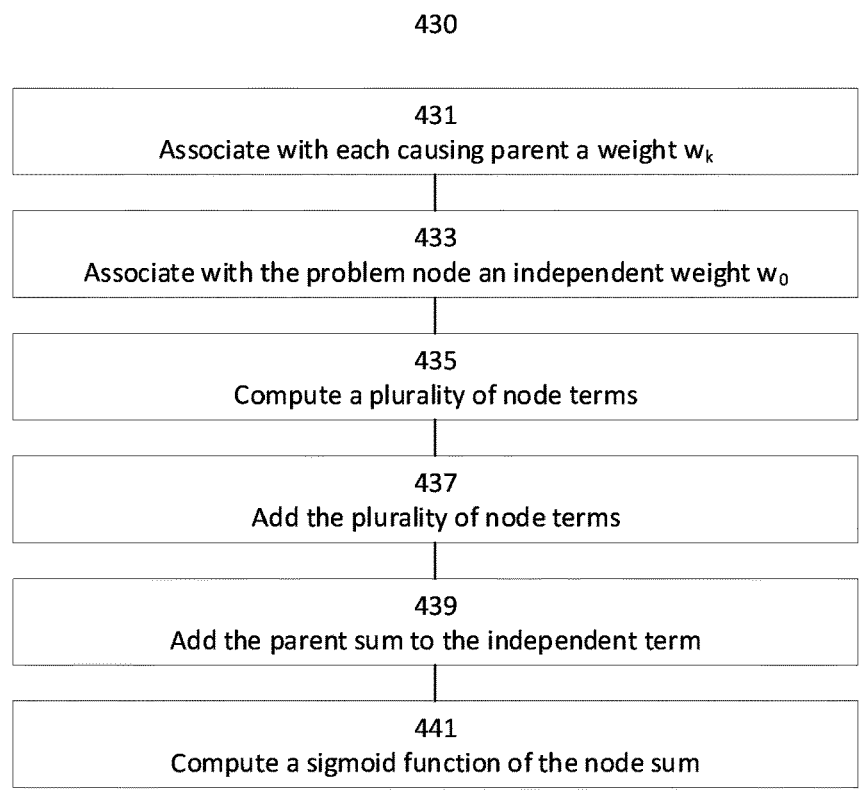

Reference is now made also to FIGS. 7A and 7B, showing flowcharts schematically representing another optional flow of operations for defining a local probability model. Reference is made to FIG. 7A, showing a flowchart schematically representing an optional flow of operations 400 for defining a local probability model for a node representing a problem, according to some embodiments of the present invention. In such embodiments, each node of the plurality of nodes has a Boolean occurrence value indicating an occurrence of the node and a numerical value of 1 in the node's Boolean occurrence value is true, otherwise 0, and at least one hardware processor 101 assigns each node representing a problem of the plurality of identified semantic entities a local probability model defined by in 401 optionally identifying a plurality of manifesting parent nodes, such that each is a parent node connected by a manifesting edge representing a manifests relationship of the plurality of identified parent-child relationships to the problem node, in 403 optionally identifying a plurality of influencing-factor parent nodes, such that each is a parent node connected by an influencing-factor edge representing an influencing-factor relationship of the plurality of identified parent-child relationships, to the problem node, and in 405 optionally identifying a plurality of influencing combinations of a plurality of Boolean occurrence values of the plurality of influencing-factor parent nodes. Next, in 407, for each of the plurality of influencing combinations at least one hardware processor 101 optionally associates the symptom node with a logistic conditional probability distribution. Reference is made now also to FIG. 7B, showing a flowchart schematically representing an optional flow of operations 430 for defining a logistic conditional probability distribution, according to some embodiments of the present invention. In 431, at least one hardware processor 101 optionally associate with each causing parent node of the plurality of causing parent nodes a node weight modifying the local probability model, denoted by $w_k$, and in 433 optionally associates with the problem node an independent weight modifying the local probability model, denoted by $w_0$. Next, at least one hardware processor 101 optionally associates with the problem node a logistic conditional probability distribution computed by: in 435 optionally computing a plurality of node terms by for each of the plurality of causing parent node's multiplying the causing parent node's $w_k$ the causing parent node's numerical value, in 437 optionally adding the plurality of node terms to produce a parent sum, in 439 optionally adding the parent sum to the independent term to produce a node sum, and in 441 optionally computing a sigmoid function of the node sum. Optionally, the sigmoid function is a logistic function defined by the formula:

$$S(x) = \frac{e^x}{e^x + 1}$$

where e denotes the base of the natural logarithm. Optionally, training the statistical model in 214 comprises deriving values for a plurality of $w_k$ and $w_0$ values from the input data using methods as known in the art.

Figure 8:
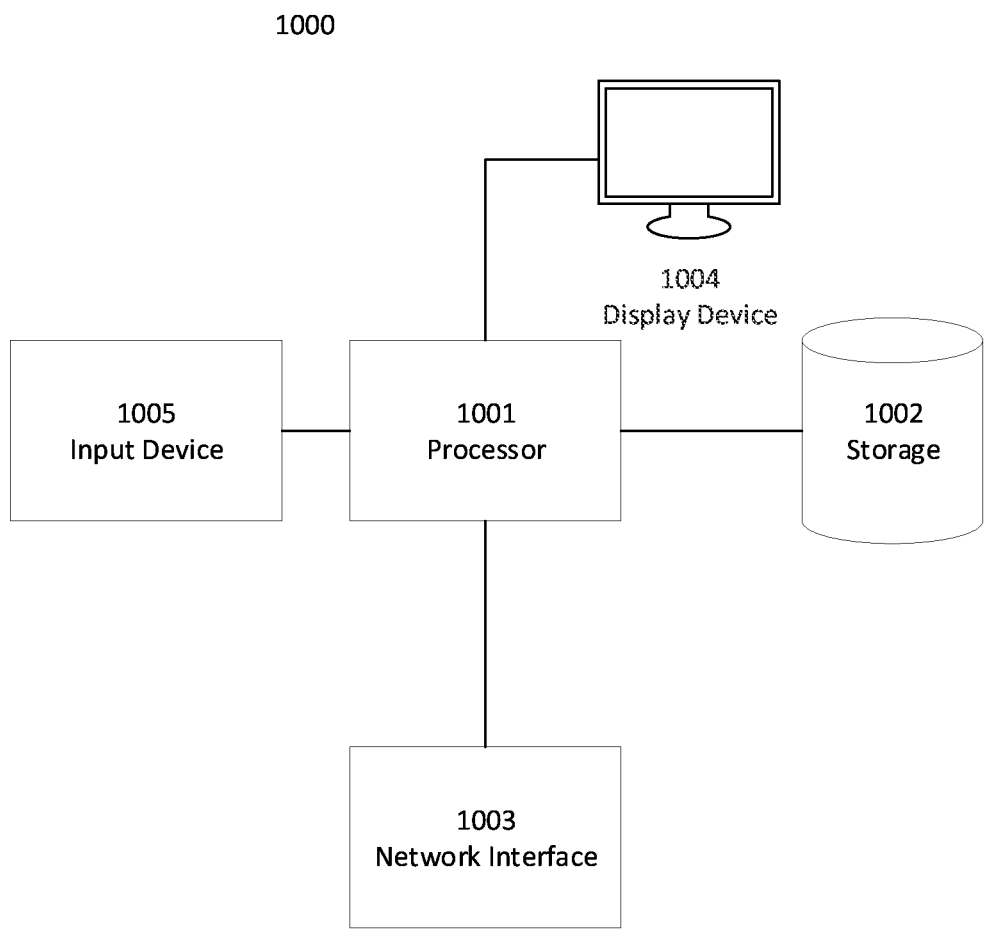
FIG. 8 is a schematic block diagram of an exemplary diagnosis system, according to some embodiments of the present invention.

In some embodiments of the present invention, a statistical model generated by system 100 is used by a fault-diagnosis system. Reference is made now also to FIG. 8, showing a schematic block diagram of an exemplary diagnosis system 1000, according to some embodiments of the present invention. In such embodiments, at least one hardware processor 1001 is connected to at least one non-volatile digital storage 1002. At least one storage 1002 is optionally used to store a statistical model received from system 100. Examples of a non-volatile digital storage are a hard disk and non-volatile random access memory (NVRAM). Optionally, at least one hardware processor 1001 is connected to at least one digital communication network interface 1003. Examples of a digital communication network interface are a wireless network interface or an Ethernet interface. Optionally, at least one hardware processor 1001 sends result digital data representing one or more possible problems to another hardware processor using at least one network interface 1003. Optionally, at least one hardware processor 1001 receives a statistical model from system 100 via at least one network interface 1003. At least one hardware processor 1001 is optionally connected to at least one display device 1004 for the purpose of displaying one or more messages comprising result digital data representing one or more possible problems. An example of a display device is a computer screen. Optionally, at least one hardware processor 1001 is connected to at least one input device 1005 for the purpose of receiving digital data comprising binary and textual representations of a plurality of observations and/or resolution digital data comprising binary and textual representations of one or more resolutions of a fault. An example of an input device is a keyboard. Optionally, at least one hardware processor receives the digital data, and additionally or alternatively, the resolution digital data via at least one network interface 1003. The digital data may be received by at least one hardware processor 1001 from a database of a customer support system and include binary and textual representations of a plurality of observations made by a person and reported by the person to the customer support system. For example, the plurality of observations may be related to an electrical appliance. The resolution data is optionally received by at least one hardware processor 1001 from the database of the customer support system.

To diagnose a fault, in some embodiments of the present invention system 1001 implements the following optional method.

Figure 9:
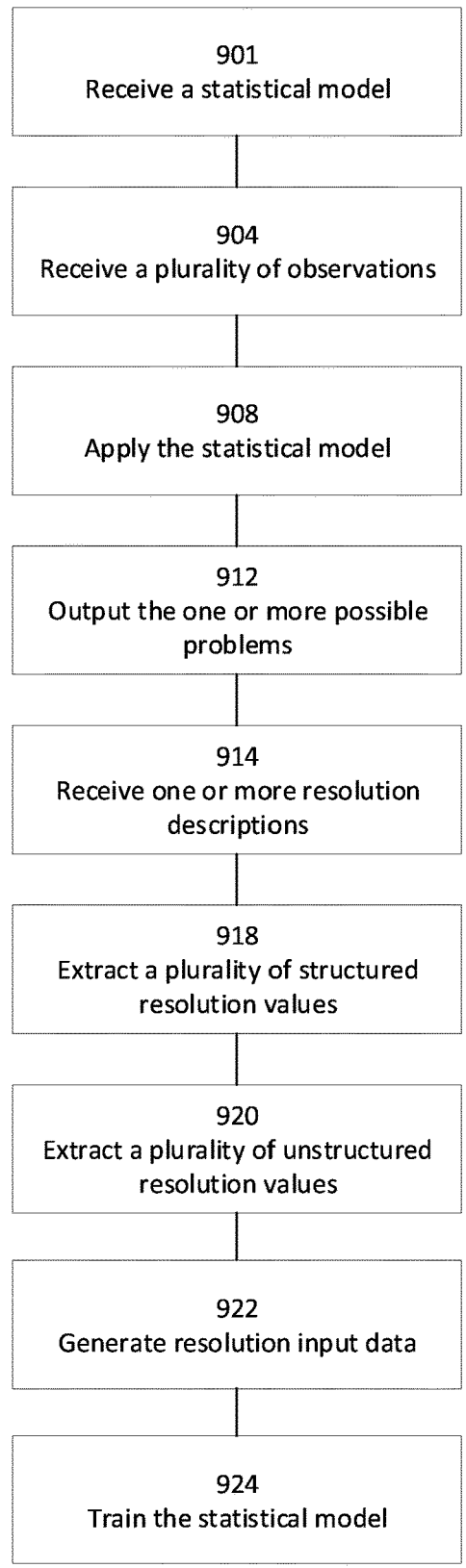
FIG. 9 is a flowchart schematically representing an optional flow of operations for fault diagnosis, according to some embodiments of the present invention.

Reference is made now also to FIG. 9, showing a flowchart schematically representing an optional flow of operations 900 for fault diagnosis, according to some embodiments of the present invention. In such embodiments, at least one hardware processor receives in 901 a statistical model generated by system 100 implementing method 200. At least one hardware processor 1001 optionally receives the statistical model via at least one network interface 1003. In 904, at least one hardware processor 1001 optionally receives a digital data comprising binary and textual representations of a plurality of observations. At least one hardware processor 1001 optionally receives the digital data via at least one input device 1005. Optionally, the digital data is stored in a database, for example in a database of a customer support system. Optionally, at least one hardware processor 1001 receives the digital data comprising the binary and textual representations of the plurality of observations via at least one network interface 1003. Optionally, the binary and textual representations of the plurality of observations comprise structured observation information organized in the identified structure, and alternatively or in addition unstructured free text observation information. In embodiments where system 1000 is used for diagnosing a fault in an electrical appliance, the plurality of observations is optionally related to an electrical appliance event. Examples of structured observation information are electrical appliance component identification values and error code values. Optionally, in 908 at least one hardware processor 1001 applies the statistical model to the digital data to identify one or more possible problems.

Figure 10:
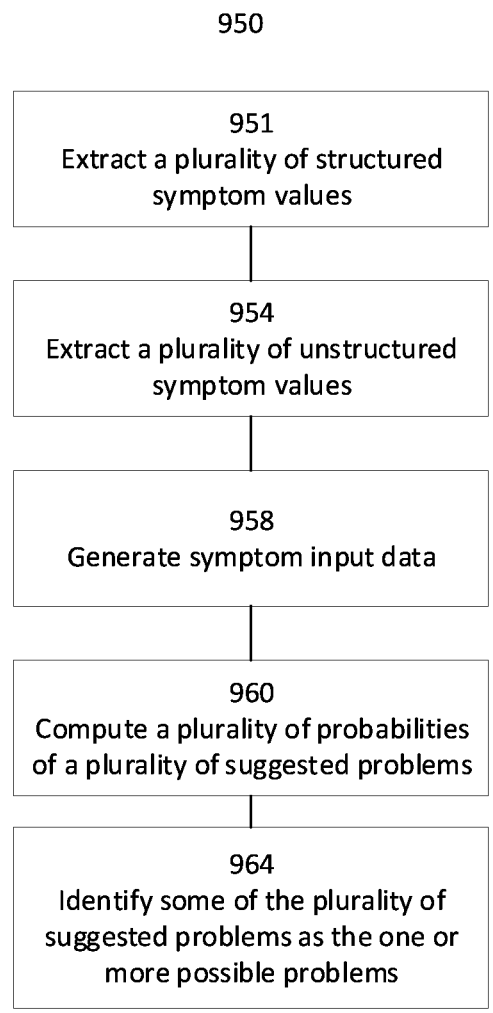
FIG. 10 is a flowchart schematically representing an optional flow of operations for applying a statistical model, according to some embodiments of the present invention.

Reference is now made also to FIG. 10, showing a flowchart schematically representing an optional flow of operations 950 for applying a statistical model, according to some embodiments of the present invention. At least one hardware processor 1001 in 951 optionally extracts a plurality of structured symptom values, each associated with at least one of the plurality of semantic entities of the plurality of semantic relationships, from the structured observation information, in 954 optionally extracts a plurality of unstructured symptom values, each associated with at least one of the plurality of semantic entities of the plurality of semantic relationships, from the unstructured free text observation information, and in 958 optionally generates symptom input data from the plurality of structured symptom values and the plurality of unstructured symptom values. Optionally, at least one hardware processor implements one or more methods similar to method 500, 600, and/or 700 in order to extract the plurality of structured symptom values in 951, to extract the plurality of unstructured symptom values in 954 and to generate the symptom input data in 958. In 960 at least one hardware processor 1001 optionally computes a plurality of probabilities of a plurality of suggested problems from the plurality of possible node values, by inputting the symptom input data to the statistical model and in 964 optionally identifies some of the plurality of suggested problems as the one or more possible problems, each possible problem optionally associated with a confidence level or probability. Optionally, at least one hardware processor 1001 identifies an identified amount of suggested problems of the plurality of suggested problems having highest probabilities as the one or more possible problems. For example, between 2 and 10 suggested problems having highest probabilities. For example, 4 suggested problems having highest probabilities.

Reference is made again to FIG. 9. In 912, at least one hardware processor 1001 optionally outputs result digital data representing the one or more possible problems, optionally to a user of the diagnosis system, for example a technician of an electrical appliance. Optionally, at least one hardware processor 1001 outputs the result digital data representing the one or more possible problems by displaying one or more messages on at least one display device 1004. Optionally, at least one hardware processor 1001 outputs result digital data representing the one or more possible problems by sending at least one message on at least one network interface 1003. Optionally, the result digital data representing the one or more problems comprises for each of the one or more possible problems a problem description and a rank value, for example a probability value.

Optionally, resolution information of an appliance event related to the observations may be used with the observations to further train the statistical model. In some embodiments, in 914 at least one hardware processor 1001 receives resolutions digital data comprising binary and textual representations of one or more resolutions of a fault, for example a fault of an electrical appliance. The comprising binary and textual representations of the one or more resolutions optionally comprise structured resolution information organized in the identified structure and alternatively or in addition unstructured resolution free text information. At least one hardware processor 1001 optionally receives the plurality of resolution digital data via at least one network interface 1003 or via at least one input device 1005. At least one hardware processor 1001 in 918 optionally extracts a plurality of structured resolution values from the structured resolution information, in 920 optionally extracts a plurality of unstructured resolutions values from the unstructured free text resolution information, and in 922 optionally generates event input data from the plurality of structured resolution values and the plurality of unstructured resolution values. Optionally, at least one hardware processor implements one or more methods similar to method 500, 600, and/or 700 in order to extract the plurality of structured resolution values in 918, to extract the plurality of unstructured resolution values in 920 and to generate the event input data in 922. Optionally, in 922 at least one hardware processor 1001 generates the event input data from the plurality of structured symptom values, the plurality of unstructured symptom values, the plurality of structured resolution values, and the plurality of unstructured resolutions values. Next, in 924, at least one hardware processor 1001 optionally trains the statistical model by inputting the event input data into the statistical model. Optionally, at least one hardware processor 1001 trains the statistical model in a plurality of iterations, using a plurality of one or more observations and a plurality of one or more resolutions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant "possible node values" and parent-child relationships will be developed and the scope of the terms "possible node value" and "parent-child relationship" are intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for generating a statistical model for fault diagnosis, comprising:

At least one hardware processor, adapted to:

extract a plurality of structured values, each associated with at least one of a plurality of semantic entities of a semantic model or at least one of a plurality of semantic relationships of the semantic model, from structured historical information organized in an identified structure and related to at least some of a plurality of historical events, the semantic model comprising said plurality of semantic entities, each corresponding to at least one entity of an ontology of an identified diagnosis domain, and each of the plurality of semantic relationships is a directional relationship assigning a source semantic entity to a destination semantic entity of the respective relationship, extract a plurality of unstructured values, each associated with at least one of the plurality of semantic entities or the plurality of semantic relationships, from unstructured historical free text information related to at least some of the plurality of historical events;

generate input data to train the statistical model, derived from the semantic model, from the plurality of structured values and the plurality of unstructured values;

train the statistical model by inputting thereto the input data; and output the statistical model for use in a system for processing digital data comprising a plurality of representations of a plurality of observations related to the identified diagnosis domain, each representation selected from a group comprising a digital representation and a textual representation for the purpose of diagnosing a fault in a diagnosable entity of the identified diagnosis domain;

wherein some of the plurality of semantic entities are each a member of a group of identified semantic entities consisting of: at least on observable phenomenon (a symptom), at least one dysfunction (a problem), at least one factor influencing a probability of a structural or functional relationship between two of the plurality of semantic entities (an influencing-factor), at least one symptom detail (an issue), and at least one location;

wherein each of the plurality of semantic relationships is a member of a group of consisting of: a causes relationship, a manifests relationship, an influences relationship, and a location-of relationship;

wherein the statistical mode comprises a plurality of nodes, each representing one of some of the plurality of semantic entities, connected by a plurality of edges, each representing one of some of the plurality of semantic relationships;

wherein the some of the plurality of semantic entities are each one of a group consisting of: a problem of the group of identified semantic entities, a symptom of the group of identified semantic entities, and an identifying-factor of the group of identified semantic entities;

wherein the some of the plurality of semantic relations are each one of a group consisting of: a cause relationship of the group of relationships, a manifests relationship of the group of relationships, an influences relationship of the group of relationships;

wherein each of the plurality of nodes has a Boolean occurrence value indicating an occurrence of the node;

wherein every symptom node of the plurality of nodes, representing a symptom of the plurality of identified semantic entities, is assigned a local probability model defined by:

identifying a plurality of manifesting parent nodes such that each is a source node connected by a manifesting edge, representing a manifests relationship of the group of relationships, to the symptom node;

identifying a plurality of influencing-factor source nodes such that each is a source node connected by an influencing-factor edge, representing an influencing-factor relationship of the group of relationships, to the symptom node;

identifying a plurality of influencing combinations of a plurality of Boolean occurrence values of the plurality of influencing-factor source nodes; and for each influencing combination of the plurality of influencing combinations:

associating with each manifesting source node of the plurality of manifesting source nodes a probability that a true Boolean occurrence value of the manifesting source node does not cause a true Boolean occurrence value of the symptom node, denoted by $\lambda.w$;

associating with the symptom node a probability that the symptom node has a true Boolean occurrence value when none of the plurality of manifesting source nodes has a true Boolean occurrence value, denoted by $\lambda.0$; and associating with the symptom node a noisy—or distribution computed by:

computing a plurality of node terms by for each of the plurality of manifesting source nodes having a true Boolean occurrence value subtracting the manifesting source node's $\lambda.w$ from 1;

multiplying the plurality of node terms to produce a parent product;

computing an independent term by subtracting $\lambda.0$ from 1;

multiplying the parent product by the independent term to produce a node product; and subtracting the node product from 1; and wherein training the statistical model comprises deriving values for a plurality of $\lambda.w$ and $\lambda.0$ values from the input data.

2. The system of claim 1, wherein the identified diagnosis domain is diagnosis of an electrical appliance;

wherein the diagnosable entity is the electrical appliance;

wherein the plurality of historical events is a plurality of historical electrical appliance events; and wherein each of the plurality of semantic entities relates to at least one of a group consisting of: the electrical appliance's structure, the electrical appliance's functionality, and the electrical appliance's environment.

3. The system of claim 1, wherein each causes relationship of the group of relationships connects a source semantic entity of problem type of the group of identified semantic entities with a destination semantic entity of said problem type of the group of identified semantic entities;

wherein each manifests relationship of the group of relationships connects a source semantic entity of a problem type of the group of identified semantic entities with a destination semantic entity of a symptom type of the group of identified semantic entities; and wherein each influences relationship of the group of relationships connects a source semantic entity of an influencing-factor type of the group of identified semantic entities with a destination semantic entity of said problem type of the group of identified semantic entities or a destination semantic entity of the symptom type of the group of identified semantic entities.

4. The system of claim 1, wherein each location-of relationship of the group of relationships connects a source semantic entity of an issue type of the group of identified semantic entities with a destination semantic entity of a location type of the group of identified semantic entities; and wherein some of the group of identified semantic entities, each selected from a group comprising a symptom of the group of identified semantic entities and a problem of the group of identified semantic entities, is mapped to a group consisting of one or more pairs of semantic entities of the group of identified semantic entities, each pair consisting of an issue of the group of identified semantic entities and a location of the group of identified semantic entities connected by the location-of relationship of the group of relationships.

5. The system of claim 1, wherein the at least one hardware processor is adapted to output the statistical model by storing the statistical model on a non-volatile digital storage connected to the at least one hardware processor or by sending the statistical model to at least one other hardware processor via at least one digital communication network interface connected to the at least one hardware processor.

6. The system of claim 1, wherein the statistical model is a Bayesian network.

7. The system of claim 2, wherein the identified structure comprises a plurality of component identifiers of one or more components of the electrical appliance.

8. The system of claim 1, wherein the at least one hardware processor is further adapted to receive the structured historical information and the unstructured historical free text information by reading the structured historical information and the unstructured historical free text information from a non-volatile digital storage connected to the at least one hardware processor.

9. The system of claim 1, wherein the at least one hardware processor is further adapted to receive the structured historical information and the unstructured historical free text information via at least one digital communication network interface connected to the at least one hardware processor.

10. The system of claim 1, wherein the identified diagnosis domain is diagnosis of a medical condition;
wherein the diagnosable entity is a patient;
wherein the plurality of historical events is a plurality of historical medical events; and
wherein each of the plurality of semantic entities relates to a medical term of a medical ontology.

11. A system for generating a statistical model for fault diagnosis, comprising:
At least one hardware processor, adapted to:
extract a plurality of structured values, each associated with at least one of a plurality of semantic entities of a semantic model or at least one of a plurality of semantic relationships of the semantic model, from structured historical information organized in an identified structure and related to at least some of a plurality of historical events, the semantic model comprising said plurality of semantic entities, each corresponding to at least one entity of an ontology of an identified diagnosis domain, and each of the plurality of semantic relationships is a directional relationship assigning a source semantic entity to a destination semantic entity of the respective relationship,
extract a plurality of unstructured values, each associated with at least one of the plurality of semantic entities or the plurality of semantic relationships, from unstructured historical free text information related to at least some of the plurality of historical events;
generate input data to train the statistical model, derived from the semantic model, from the plurality of structured values and the plurality of unstructured values;
train the statistical model by inputting thereto the input data; and
output the statistical model for use in a system for processing digital data comprising a plurality of representations of a plurality of observations related to the identified diagnosis domain, each representation selected from a group comprising a digital representation and a textual representation for the purpose of diagnosing a fault in a diagnosable entity of the identified diagnosis domain;
wherein some of the plurality of semantic entities are each a member of a group of identified semantic entities consisting of: at least on observable phenomenon (a symptom), at least one dysfunction (a problem), at least one facto influencing a probability of a structural or functional relationship between two of the plurality of semantic entities (an influencing-factor), at least one symptom detail (an issue), and at least one location;
wherein each of the plurality of semantic relationships is a member of a group of consisting of: a causes relationship, a manifests relationship, an influences relationship, and a location-of relationship;
wherein the statistical mode comprises a plurality of nodes, each representing of some of the plurality of semantic entities, connected by a plurality of edges, each representing one of some of the plurality of semantic relationships;
wherein the some of the plurality of semantic entities are each one of a group consisting of: a problem of the group of identified semantic entities, a symptom of the group of identified semantic entities, and an identifying-factor of the group of identified semantic entities;
wherein the some of the plurality of semantic relations are each one of a group consisting of: a cause relationship of the group of relationships, a manifests relationship of the group of relationships, an influences relationship of the group of relationships;
wherein each of the plurality of nodes has a Boolean occurrence value indicating an occurrence of the node;
wherein each node having a true Boolean occurrence value has a numerical value of 1, otherwise a numerical value of 0;
wherein every problem node of the plurality of nodes, representing a problem of the plurality of identified semantic entities, is assigned a local probability model defined by:
identifying a plurality of causing source nodes such that each is a source node connected by a causing edge, representing a causes relationship of the group of relationships, to the problem node;
identifying a plurality of influencing-factor source nodes such that each is a source node connected by an influencing-factor edge, representing an influencing-factor relationship of the group of relationships, to the problem node;
identifying a plurality of influencing combinations of a plurality of Boolean occurrence values of the plurality of influencing-factor source nodes; and
for each influencing combination of the plurality of influencing combinations:
associating with each causing source node of the plurality of causing source nodes a node weight modifying the local probability model, denoted by wk;
associating with the problem node an independent weight modifying the local probability model, denoted by w0; and associating with the problem node a logistic conditional probability distribution computed by:
  computing a plurality of node terms by for each of the plurality of causing source node's multiplying the causing source node's wk by the causing source node's numerical value;
  adding the plurality of node terms to produce a parent sum;
  adding the parent sum to the independent weight to produce a node sum; and
  computing a sigmoid function of the node sum; and
wherein training the statistical model comprises deriving values for a plurality of wk and w0 values from the input data.

* * * * *